United States Patent [19]

Baur et al.

[11] Patent Number: 4,827,014

[45] Date of Patent: May 2, 1989

[54] 2-HYDROXY-3-AMINOPROPIONIC-N,N-DIACETIC ACID AND DERIVATIVES THEREOF, PREPARATION THEREOF, AND DETERGENTS CONTAINING SAME

[75] Inventors: Richard Baur, Mutterstadt; Felix Richter, Bruel; Stefan Birnbach, Ludwigshafen; Rolf Fikentscher, Ludwigshafen; Alfred Oftring, Ludwigshafen; Ekhard Winkler, Mutterstadt; Werner Bochnitschek, Ludwigshafen, all of Fed. Rep. of Germany

[73] Assignee: BASF Aktiengesellschaft, Ludwigshafen, Fed. Rep. of Germany

[21] Appl. No.: 177,084

[22] Filed: Apr. 4, 1988

[30] Foreign Application Priority Data

Apr. 11, 1987 [DE] Fed. Rep. of Germany ....... 3712330

[51] Int. Cl.$^4$ .................. C07C 101/20; C07C 101/30
[52] U.S. Cl. ..................... 558/441; 558/445; 560/170; 562/567; 562/568; 562/571
[58] Field of Search ............... 558/441, 445; 560/170; 562/567, 568, 571; 252/DIG. 11

[56] References Cited

U.S. PATENT DOCUMENTS 3,725,473  4/1973  Sundby ........................... 260/534 E
3,962,319  6/1976  Becke ............................... 260/514 J

*Primary Examiner*—Paul Lieberman
*Assistant Examiner*—Kathleen Markowski
*Attorney, Agent, or Firm*—Oblon, Fisher, Spivak, McClelland & Maier

[57] ABSTRACT

2-Hydroxy-3-aminopropionic-N,N-diacetic acid and derivatives thereof are used in particular as complexing agents, bleaching agent stabilizers and builders in detergents.

6 Claims, No Drawings

2-HYDROXY-3-AMINOPROPIONIC-N,N-DIACETIC ACID AND DERIVATIVES THEREOF, PREPARATION THEREOF, AND DETERGENTS CONTAINING SAME

The present invention relates to 2-hydroxy-3-aminopropionic-N,N-diacetic acid and derivatives thereof, to the preparation thereof, to the use thereof in particular as complexing agents, bleaching agent stabilizers and builders in detergents, and to detergents containing same.

Complexing agents for alkaline earth and other metal ions, for example of calcium, magnesium, iron, manganese and copper, are required for a wide range of technical fields.

Examples of fields of application and end-uses are detergents in general industry, in electroplating, in water treatment and in polymerizations, the photographic industry, the textile industry and the paper industry and also various uses in pharmaceuticals, cosmetics, foodstuffs and plant nutrition.

Examples of conventional acknowledged complexing agents, in particular for detergents, are nitrilotriacetic acid (NTA), ethylenediaminetetraacetic acid.(EDTA), ethylenediaminetetramethylenephosphonic acid (EDTMP), propylenediaminetetraacetic acid (PDTA), hydroxypropylenediaminetetraacetic acid (HPDTA), hydroxyethanediphosphonic acid, diethylenetriaminetetraacetic acid, diethylenetriaminetetramethylenephosphonic acid, hydroxyethylimino, diacetic acid, hydroxyethylethylenediaminetriacetic acid diethylenetriaminepentaacetic acid and also for example diethanolglycine, ethanolglycine, citric acid, glucoheptonic acid or tartaric acid, as found for example under the heading of Waschmittel in Ullmann's Encyklopädie der technischen Chemie, 4th edition, volume 24, pages 63–160, in particular pages 91–96, Verlag Chemie, Weinheim, 1983.

The action of the existing compounds, some of which are used on a large scale, is not always optimal in a particular case. For instance, NTA makes a very good complexing agent and, in detergents, a fairly good builder for improving the whitening effect and for preventing deposits which cause incrustations and graying on the fabric. However, its performance as a bleaching agent stabilizer is comparatively poor. Even EDTA, despite its good complexing action toward heavy metals, is only a moderate bleaching agent stabilizer in detergents.

In some cases, the biodegradability also leaves something to be desired. For instance, EDTA turns out to be insufficiently biodegradable in conventional tests, as do PDTA, HPDTA and corresponding aminomethylenephosphonates which, furthermore, are frequently undesirable on account of their phosphorus content.

A paper by L. Erdey et al. in Acta Chim. Hung. 21 (1959), 327-32, describes the complexing properties of 2,3-dihydroxypropylamine-N,N-diacetic acid, serine-N,N-diacetic acid prepared from D,L-serine and chloracetic acid, and L-glutamic-N,N-diacetic acid with regard to the stability of complexes formed with alkaline earth metal ions. In respect of the serine-N,N-diacetic acid complexes formed with alkaline earth metal ions it is stated in said paper that their stability is lower than expected since it was thought that the stability ratings of nitrilotriacetic acid should be obtainable.

The usefulness of these compounds as auxiliary complexing agents was studied by adding them to zinc, iron(III), copper and nickel solutions, in each case at pH 13.5, and also to aluminum solutions at pH 7. In respect of serine-N,N-diacetic acid it is found here that it keeps zinc and copper ions in solution at a molar ratio of metal ion:complexing agent of 1:2, excess metal ions being precipitated. It is stated as a summarizing result that the investigated compounds have only very limited usefulness as volumetric solutions, ie. for the analysis of alkaline earth metal solutions, and that they may be of use as auxiliary complexing agents for heavy metal ions.

The lack of complexing power evident from these results does not suggest to the skilled worker that he should prepare 2-hydroxy-3-aminopropionic-N,N-diacetic acid (isoserine-N,N-diacetic acid) and its derivatives and use them as complexing agents.

It is an object of the present invention to provide a novel complexing agent for alkaline earth metal and heavy metal ions for a wide range of technical fields, in particular for detergents, which, in addition to having good complexing properties, is ecologically safe, ideally contains no phosphorus and is readily biodegradable. A further object is to develop an industrially advantageous process for preparing said new complexing agent.

We have found that these objects are achieved with 2-hydroxy-3-aminopropionic-N,N-diacetic acid and its derivatives of the formula I

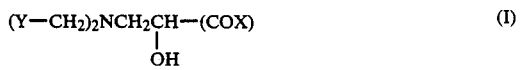

$$(Y-CH_2)_2NCH_2CH-(COX) \quad\quad (I)$$
$$\underset{OH}{|}$$

where Y is a —COOH radical, which may be present in the form of an alkali metal, ammonium or substituted ammonium salt, a —COOR$^1$ radical where R$^1$ is alkyl of 1 to 4 carbon atoms, or a —CN radical, and X is hydroxyl, in which case the then resulting carboxyl may be present in the form of an alkali metal, ammonium or substituted ammonium salt, an —OR$^2$ radical where R$^2$ is alkyl of 1 to 4 carbon atoms, or an —NR$^3$R$^4$ radical where R$^3$ and R$^4$ are identical or different and each is hydrogen or alkyl of 1 to 4 carbon atoms, which, in the form of the free acid or in particular as sodium, potassium, ammonium or organic amine salts, are outstanding novel complexing agents, in particular for calcium, magnesium and iron, copper, nickel and manganese ions, while the acid derivatives, such as esters, amides and nitriles, are preferably intermediates for preparing the acid and its salts.

The present invention therefore provides as preferred a novel heavy metal and alkaline earth metal ion complexing agent of the formula I where Y is —COOH and X is —OH, in which the carboxyl groups may be present in the form of alkali metal, ammonium or substituted ammonium salts.

Specific examples are the free 2-hydroxy-3-aminopropionic-N,N-diacetic acid, the sodium, potassium and ammonium salts, in particular the trisodium, tripotassium and triammonium salt, and also organic triamine salts containing a tertiary nitrogen atom.

The organic amine salts can be derived from bases comprising in particular tertiary amines, such as trialkylamines of 1 to 4 carbon atoms in the alkyl, such as trimethylamine and triethylamine, and trialkanolamines having 2 or 3 carbon atoms in the alkanol moiety, preferably triethanolamine and tripropanolamine.

The compounds of the formula I can be prepared by reacting a compound of the formula II

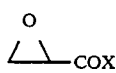  (II)

where X has the meanings indicated for the formula I, with a compound of the formula III $HN(CH_2-Y)_2$  (III)

where Y has the meanings mentioned for the formula I, in water, in an organic solvent or in a mixture thereof at from 10° to 80° C. and, if as the case may be amide, ester or nitrile groups are present, hydrolyzing these in the presence of an acid or base and as desired isolating the free acid or a salt conforming to the formula I.

The starting compounds used of the formulae II and III are known or can be prepared without special problems in a conventional manner.

Preferred starting compounds of the formula II are glycidic acid, if desired in the form of the sodium, potassium or ammonium salt, glycidamide or a glycidic ester with a monohydric alcohol of 1 to 4 carbon atoms.

Starting compounds of the formula III preferably comprise iminodiacetic acid, if desired in the form of the mono- or di-sodium, -potassium or -ammonium salts, iminodiacetonitrile, methyl iminodiacetate and ethyl iminodiacetate.

The starting compounds of the formulae II and III are preferably reacted in equimolar amounts.

The solvents used are preferably water or water-miscible organic solvents, such as methanol, ethanol, n-propanol, isopropanol, tertiary butanol, dioxane and tetrahydrofuran. It is also possible to use mixtures of these organic solvents with each other or with water. In the case of aqueous mixtures, advantageously a quantity of water is mixed with from 10 to 70% of its weight of organic solvent. If desired, the reaction can also be carried out without solvent, for example if the starting material is a liquid ester, such as a glycidic ester or an iminodiacetic diester.

The concentration of the starting materials in the particular solvent is advantageously 10–80% by weight, preferably 20–70% by weight.

The reaction is advantageously carried out at from 10° to 80° C., preferably at from 40° to 70° C.

The reaction is advantageously carried out at from pH 4 to 10, preferably at from pH 6 to 9. The reaction is possible under atmospheric pressure or else under superatmospheric pressure.

If amide, ester or nitrile groups are present, a hydrolysis to give the tricarboxylic acid is carried out in a conventional manner in an aqueous reaction mixture in the presence of an alkali, such as sodium hydroxide or potassium hydroxide or of an acid, such as sulfuric acid or hydrochloric acid, with or without the addition of water.

This hydrolysis is advantageously carried out at from 20° to 110° C., preferably at from 40° to 100° C., in the presence of a possibly small excess of base or acid.

Depending on the reaction conditions, the product obtained is preferably 2-hydroxy-3-ainopropionic-N,N-diacetic acid or an alkali metal salt. Subsequently, it presents no problem to prepare a salt with another cation.

If necessary, it is also possible, conversely, to turn the acid obtained into an acid derivative in a conventional manner.

The compounds of the formula I can be isolated in a pure form without difficulties. Suitable ways of obtaining the free acid and the salts are in particular spray or freeze drying, crystallization or precipitation. It can be advantageous to use the solution obtained directly in an industrial application.

In further processes, the compounds of the formula I can be prepared by reacting 1 mole of 2-hydroxy-3-aminopropionic acid, if desired in the form of an alkali metal salt, of an alkyl ester of 1 to 4 carbon atoms in the alkyl or of the amide, unsubstituted or mono- or disubstituted on the amide nitrogen by alkyl of 1 to 4 carbon atoms, in water, in an organic solvent or in a mixture thereof at from 0° to 100° C. with from 2.0 to 2.6 moles of a monohaloacetic acid, an alkyl monohaloacetate of 1 to 4 carbon atoms in the alkyl or monohaloacetonitrile in an alkaline medium or in the presence of an acid acceptor and hydrolyzing any amide, ester and nitrile groups present in the presence of an acid or base and as desired isolating the free acid or a salt conforming to the formula I.

In a further process for preparing compounds of the formula I where Y has the meanings indicated for the formula I other than $-COOR^1$ and X has the meanings indicated for the formula I, 1 mole of 2-hydroxy-3-aminopropionic acid, if desired in the form of an alkali metal salt, of an alkyl ester of 1 to 4 carbon atoms in the alkyl or of the amide, unsubstituted or mono- or disubstituted on the amide nitrogen by alkyl of 1 to 4 carbon atoms, is reacted in water, in an organic solvent or in a mixture thereof with from 2.0 to 2.6 moles of formaldehyde and from 2 to 2.3 moles of liquid hydrocyanic acid at from 0° to 45° C. or with from 2 to 2.3 moles of alkali metal cyanide at from 40° to 100° C. and hydrolyzing any amide, ester and nitrile groups present in the presence of an acid or base and as desired isolating the free acid or a salt conforming to the formula I.

In these processes, the preferred alkali metal salts of 2-hydroxy-3-aminopropionic acid are the sodium and the potassium salts.

The preparation of 2-hydroxy-3-aminopropionic acid for use as a starting compound is advantageously effected by reacting a glycidyl compound of the formula II, preferably glycidic acid, its sodium or potassium salt, glycidamide or an ester thereof in an aqueous, organic or aqueous-organic solution, as specified above, with from 1 to 2 moles, preferably with from 1 to 1.4 moles, of ammonia per mole of glycidyl compound of the formula II at from 10° to 80° C. and at from pH 6 to 9.

If the reaction is carried out with a monohaloacetic acid compound, preference is given to chloroacetic acid or bromoacetic acid and temperatures from 40° to 80° C. The alkaline medium can comprise the above-mentioned solvents or mixtures, although preference is given to an aqueous solution at from pH 7.5 to 12, advantageously set with NaOH or KOH, so that the salts are present, or to the presence of preferably a tertiary amine as acid acceptor. Advantageous tertiary amines are trialkylamines having 1 to 4 carbon atoms in the alkyl, such as trimethylamine, triethylamine, tri-n-propylamine, triisopropylamine, tri-n-butylamine and triisobutylamine, and also cyclic tertiary amines, such as 1,4-diazabicyclo[2.2.2]octane.

In an advantageous process in the manner of a conventional Strecker synthesis (cf. Houben-Weyl, vol.

11/2, pp. 408–412 (1958), Thieme-Verlag Stuttgart), the sodium or potassium salt of 2-hydroxy-3-aminopropionic acid is reacted in one of the abovementioned solvents or solvent mixtures, preferably in an aqueous solution, with the formaldehyde in the form of an aqueous approximately 30% strength by weight solution thereof and liquid hydrocyanic acid preferably at from 15° to 25° C. The reaction with an alkali metal cyanide, i.e. sodium cyanide or potassium cyanide, in place of liquid hydrocyanic acid is preferably carried out at from 70° to 100° C.

The reaction with free hydrocyanic acid is advantageously carried out in the pH range from 0 to 11, preferably from 3 to 9.

The hydrolysis which may be necessary if ester, amide and nitrile groups are present and the isolation of the acid or salts are carried out as indicated above.

In a further process for preparing compounds of the general formula I, 1 mole of α-chloroacrylic acid, if desired in the form of an alkali metal salt, in particular the Na salt, or of an alkyl ester of 1 to 4 carbon atoms, is reacted in water, in an organic solvent or in a mixture thereof with from 1.0 to 1.2 moles of a compound of the general formula III at from 20° to 150° C. and any ester and/or nitrile groups present and the chlorine still present are conventionally hydrolyzed in the presence of a base and replaced by OH and the free acid or a salt according to the formula I is isolated.

This invention represents the first time that 2-hydroxy-3-aminopropionic-N,N-diacetic acid had been prepared, and this acid and its salts are highly suitable for complexing alkaline earth metal and heavy metal ions. Owing to this capability, the acid and its salts have a large number of possible uses in industry. Since they are compounds which are very readily biodegradable, they can be used in large amounts wherever wastewaters need to be treated and, what is more, phosphorus-containing compounds are to be avoided.

In detergents the complexing agents according to the invention can be used to control the level of free heavy metal ions in the detergents themselves and in wash liquors prepared therefrom. The amount used if used as a complexing agent is advantageously from 0.1 to 2%, based on the total weight of the detergent constituents.

Their advantageous action also includes bleaching agent stabilization, for example for sodium perborate, in detergents and in the bleaching of textiles, pulp or paper stock. Traces of heavy metals, such as iron, copper and manganese, are present in the washing powder itself, in the water and in the textile material and they catalyze the decomposition of the sodium perborate. The complexing agents according to the invention bind these metal ions and prevent the undesirable decomposition of the bleaching system during storage and in the wash liquor. This enhances the efficiency of the bleaching system and reduces fiber damage.

In addition, enzymes, optical brighteners and scents are protected from heavy metal catalyzed oxidative decomposition.

In liquid detergent formulations the novel complexing agents can be used as preservatives advantageously in an amount from 0.05 to 1% by weight, based on the total weight of the detergent formulation.

In soaps the novel complexing agents prevent for example metal catalyzed oxidative decompositions.

Furthermore, they give excellent performance in detergents as builders for preventing precipitates and incrustations on the fabric.

They can be used with advantage wherever in industrial processes precipitates of Ca, Mg and heavy metal salts are a nuisance and are to be prevented. So they are used for example for preventing scale deposits and incrustations in kettles, pipelines, spray nozzles or generally on smooth surfaces.

They can be used for stabilizing phosphates in alkaline degreasing baths and to prevent the precipitation of lime soaps and as a result prevent the tarnishing of nonferrous surfaces and prolong the service lives of alkaline cleaning baths.

They can be used as complexing agents in alkaline derusting and descaling baths and also in electroplating baths in place of cyanides as sequestrants of impurities.

The treatment of cooling water with the novel complexing agents prevents and redissolves scale deposits. Of advantage is the use in an alkaline medium, thereby removing corrosion problems.

In the polymerization of rubber they can be used for preparing the redox catalysts used therein. They additionally prevent the precipitation of iron hydroxide in the alkaline polymerization medium.

In the photographic industry the novel complexing agents can be used in developer/fixing baths made up with hard water to prevent the precipitation of sparingly soluble Ca- and Mg-salts. The precipitations lead to fogging on films and photographs and also to deposits in the tanks, which are thus advantageously avoidable. Iron(III)-complexing solutions can advantageously be used in bleach fixing baths to replace the ecologically unsafe hexacyanoferrate solutions.

In the textile industry they can be used for removing heavy metal traces during the manufacture and dyeing of natural and synthetic fibers, thereby preventing many problems, such as dirt spots and stripes on the textile material, loss of luster, poor wettability, unlevelness and off-shade dyeings.

In the paper industry they can be used for eliminating heavy metal/iron ions. Iron deposits on paper lead to hot spots where the oxidative, catalytic decomposition of the cellulose starts.

Examples of various uses are applications in pharmaceuticals, cosmetics and foodstuffs where the metal catalyzed oxidation of olefinic double bonds and hence the rancidification of goods is prevented.

In plant nutrition, heavy metal deficiencies are remedied by using Cu, Fe, Mn, Zn complexes. Heavy metals are added as chelates to prevent their precipitation in the form of biologically inactive, insoluble salts.

Further fields of application for the novel complexing agents are flue gas washing, specifically the removal of $NO_x$ from flue gases, $H_2S$ oxidation, metal extraction and uses as catalysts for organic syntheses (for example air oxidation of paraffins, hydroformylation of olefins to alcohols).

The complexing agents for alkaline earth metal and heavy metal ions according to the invention are used as complexing agents in general and specifically in detergents and also rinse and wash assistants, in particular as complexing agents for heavy metal and/or alkaline earth metal ions, as bleaching agent stabilizers and as builders.

The present invention accordingly provides the corresponding uses and detergents which contain these compounds as well as the customary constituents known to those skilled in the art.

The compounds to be used according to the invention are used in detergent formulations in general in an amount from 0.01 to 20% by weight, preferably from 0.05 to 10% by weight, based on the total weight of the detergent formulation.

If specifically used as a builder, amounts from 1 to 10% by weight are particularly preferred, while if specifically used as a bleaching agent stabilizer for perborates, amounts from 0.05 to 1% by weight are particularly preferred. If used specifically as a complexing agent in detergents, amounts from 0.01 to 2% by weight are preferred.

Detergent formulations which, based on the total weight, contain from 0.01 to 20, preferably from 0.05 to 10, % by weight of compound to be used according to the invention generally contain as additional constituents, based on the total weight, from 6 to 25% by weight of surfactants, from 15 to 50% by weight of builders with or without cobuilders, from 5 to 35% by weight of bleaching agents with or without bleaching agent activators, and from 3 to 30% by weight of assistants, such as enzymes, foam regulants, corrosion inhibitors, optical brighteners, scents, dyes or formulation aids, eg. sodium sulfate.

The compounds according to the invention can also be used as complexing agents, builders and bleaching agent stabilizers in detergent formulations together with other, prior art agents, in which case the general properties can be substantially improved in respect of sequestration, incrustation inhibition, grayness inhibition, primary washing action and bleaching action.

In what follows, the customary constituents of detergent formulations referred to above in general terms are recited in terms of examples:

Suitable surfactants are those which contain in the molecule one or more hydrophobic organic radicals and one or more water-solubilizing anionic, zwitterionic or nonionic groups. The hydrophobic radicals usually are aliphatic hydrocarbyl of 8 to 26, preferably 10 to 22, in particular 12 to 18, carbon atoms or aromatic alkyl having 6 to 18, preferably 8 to 16, aliphatic carbon atoms.

Suitable synthetic anionic surfactants are in particular those of the sulfonate, sulfate or synthetic carboxylate type.

Suitable surfactants of the sulfonate type are alkylbenzenesulfonates having 4 to 15 carbon atoms in the alkyl, mixtures of alkene- and hydroxyalkane-sulfonates and also -disulfonates as obtained for example from monoolefins having a terminal or nonterminal double bond by sulfonation with gaseous sulfur trioxide and subsequent alkaline or acid hydrolysis of the sulfonation products. Also suitable are alkanesulfonates obtainable from alkanes by sulfochlorination or sulfoxidation and subsequent hydrolysis or neutralization or by bisulfite addition onto olefins. Further useful surfactants of the sulfonate type are the esters of α-sulfo fatty acids, for example the α-sulfonic acids of hydrogenated methyl or ethyl esters of coconut, palm kernel or tallow fat acid.

Suitable surfactants of the sulfate type are the sulfuric monoesters of primary alcohols, for example coconut fat alcohols, tallow fat alcohols or oleyl alcohol, and those of secondary alcohols. Also suitable are sulfated fatty acid alkanolamines, fatty acid monoglycerides or reaction products of from 1 to 4 moles of ethylene oxide with primary or secondary fatty alcohols or alkylphenols.

Further suitable anionic surfactants are the fatty acid esters or fatty amides of hydroxy- or amino-carboxylic or -sulfonic acids, for example the fatty acid sarcosides, glycolates, lactates, taurides or isothionates.

Anionic surfactants can be present in the form of their sodium, potassium and ammonium salts and also as soluble salts of organic bases, such as mono-, di- or triethanolamine. Also possible are ordinary soaps, i.e. salts of natural fatty acids.

Suitable nonionic surfactants (nonionics) are for example adducts of from 3 to 40, preferably 4 to 20, moles of ethylene oxide on 1 mole of fatty alcohol, alkylphenol, fatty acid, fatty amine, fatty acid amide or alkanesulfonamide. Of particular importance are the adducts of from 5 to 16 moles of ethylene oxide on coconut or tallow fat alcohols, on oleyl alcohol or on synthetic alcohols of 8 to 18, preferaly 12 to 18, carbon atoms, and also on mono- or dialkylphenols of 6 to 14 carbon atoms in the alkyl(s). Besides these water-soluble nonionics, however, it is also possible to use water-insoluble or incompletely water-soluble polyglycol ethers having 1 to 4 ethylene glycol ether radicals in the molecule, in particular if used together with water-soluble nonionic or anionic surfactants.

Further suitable nonionic surfactants are the water-soluble adducts of ethylene oxide on propylene glycol ether, alkylenediaminopolypropylene glycol and alkylpolypropylene glycol having 1 to 10 carbon atoms in the alkyl chain which contain from 20 to 250 ethylene glycol ether groups and from 10 to 100 propylene glycol ether groups and where the polypropylene glycol ether chain acts as a hydrophobic radical.

It is also possible to use nonionic surfactants of the amine oxide or sulfoxide type.

The foaming power of surfactants can be enhanced or reduced by combining suitable types of surfactants. A reduction can also be obtained by adding nonsurfactant-like organic substances.

Suitable builder substances are for example: wash alkalis, such as sodium carbonate and sodium silicate, or complexing agents, such as phosphates, or ion exchangers, such as zeolites, and mixtures thereof. These builder substances have as their function to eliminate the hardness ions, which come partly from the water, partly from dirt or the textile material, and to support the surfactant action. Aside from the abovementioned builder substances, the builder component may further contain cobuilders. In modern detergents, it is the function of cobuilders to undertake some of the functions of phosphates, eg. sequestration, soil antiredeposition and primary and secondary washing action.

The builder components may contain for example water-insoluble silicates as described for example in German Laid-Open Application DE-OS No. 2,412,837 and/or phosphates. As phosphate it is possible to use pyrophosphate, triphosphate, higher polyphosphates and metaphosphates. Similarly, phosphorus-containing organic complexing agents, such as alkanepolyphosphonic acids, amino- and hydroxy-alkanepolyphosphonic acids and phosphonocarboxylic acids, are suitable for use as further detergent ingredients. Examples of such detergent additives are the following compounds: methanediphosphonic acid, propane-1,2,3-triphosphonic acid, butane-1,2,3,4-tetraphosphonic acid, polyvinylphosphonic acid, 1-aminoethane-1,1-diphosphonic acid, 1-amino-1-phenyl-1,1-diphosphonic acid, aminotrismethylenetriphosphonic acid, methylamino- or ethylamino-bismethylenediphosphonic acid, ethylenediaminetetramethylenetetraphosphonic acid, diethylenetriaminopentamethylenepentaphosphonic acid, 1-hydroxyethane-1,1-diphosphonic acid, phosphonoacetic and phosphonopropionic acid, copolymers of vinylphosphonic acid and acrylic and/or maleic acid and also partially or completely neutralized salts thereof.

Further organic compounds which act as complexing agents for calcium and may be present in detergent formulations are polycarboxylic acids, hydroxycarboxylic acids and aminocarboxylic acids which are usually used in the form of their water-soluble salts.

Examples of polycarboxylic acids are dicarboxylic acids of the general formula $HOOC-(CH_2)_m-COOH$ where m is 0–8, and also maleic acid, methylenemalonic acid, citraconic acid, mesaconic acid, itaconic acid, noncyclic polycarboxylic acids having 3 or more carboxyl groups in the molecule, e.g. tricarballylic acid, aconitic acid, ethylenetetracarboxylic acid, 1,1,3-propanetetracarboxylic acid, 1,1,3,3,5,5-pentanehexacarboxylic acid, hexanehexacarboxylic acid, cyclic di- or polycarboxylic acids, e.g. cyclopentanetetracarboxylic acid, cyclohexanehexacarboxylic acid, tetrahydrofurantetracarboxylic acid, phthalic acid, terephthalic acid, benzene-tricarboxylic, -tetracarboxylic or -pentacarboxylic acid and mellitic acid.

Examples of hydroxymonocarboxylic and hydroxypolycarboxylic acids are glycollic acid, lactic acid, malic acid, tartronic acid, methyltartronic acid, gluconic acid, glyceric acid, citric acid, tartaric acid and salicylic acid.

Examples of aminocarboxylic acids are glycine, glycylglycine, alanine, asparagine, glutamic acid, aminobenzoic acid, iminodiacetic acid, iminotriacetic acid, hydroxyethyliminodiacetic acid, ethylenediaminotetraacetic acid, hydroxyethylethylenediaminetriacetic acid, diethylenetriaminepentaacetic acid and higher homologues which are preparable by polymerization of an N-aziridylcarboxylic acid derivative, for example of acetic acid, succinic acid or tricarballylic acid, and subsequent hydrolysis, or by condensation of polyamines having a molecular weight of from 500 to 10,000 with salts of chloroacetic or bromoacetic acid.

Preferred cobuilder substances are polymeric carboxylic acids. These polymeric carboxylic acids shall include the carboxymethyl ethers of sugars, of starch and of cellulose.

Particularly important polymeric carboxylic acids are for example the polymers of acrylic acid, maleic acid, itaconic acid, mesaconic acid, aconitic acid, methylenemalonic acid, citraconic acid and the like, the copolymers between the aforementioned carboxylic acids, for example a copolymer of acrylic acid and maleic acid in a ratio of 70:30 and having a molecular weight of 70,000, or copolymers thereof with ethylenically unsaturated compounds, such as ethylene, propylene, isobutylene, vinyl alcohol, vinyl methyl ether, furan, acrolein, vinyl acetate, acrylamide, acrylonitrile, methacrylic acid, crotonic acid and the like, e.g. the 1:1 copolymers of maleic anhydride and methyl vinyl ether having a molecular weight of 70,000 or the copolymers of maleic anhydride and ethylene and/or propylene and/or furan.

The cobuilders may further contain soil antiredeposition agents which keep the dirt detached from the fiber in suspension in the liquor and thus inhibit graying. Suitable for this purpose are water-soluble colloids usually of an organic nature, for example the water-soluble salts of polymeric carboxylic acids, glue, gelatin, salts of ethercarboxylic acids or ethersulfonic acids of starch and of cellulose or salts of acid sulfates of cellulose and of starch. Even water-soluble polyamides containing acid groups are suitable for this purpose. It is also possible to use soluble starch products and starch products other than those mentioned above, for example degraded starch, aldehyde starches and the like. Polyvinylpyrrolidone is also usable.

Bleaching agents are in particular hydrogen peroxide and derivatives thereof or available chlorine compounds. Of the bleaching agent compounds which provide $H_2O_2$ in water, sodium perborate hydrates, such as $NaBO_2.H_2O_2.3H_2O$ and $NaBO_2.H_2O_2$, are of particular importance. However, it is also possible to use other $H_2O_2$-providing borates. These compounds can be replaced in part or in full by other sources of active oxygen, in particular by peroxyhydrates, such as peroxycarbonates, peroxyphosphonates, citrate perhydrates, urea-$H_2O_2$ or melamine-$H_2O_2$ compounds and also by $H_2O_2$-providing peracid salts, for example caroates, perbenzoates or peroxyphthalates.

Aside from those according to the invention, customary water-soluble and/or water-insoluble stabilizers for peroxy compounds can be incorporated together with the former in amounts from 0.25 to 10% by weight, based on the peroxy compound. Suitable water-insoluble stabilizers are the magnesium silicates $MgO:SiO_2$ from 4:1 to 1:4, preferably from 2:1 to 1:2, in particular 1:1, in composition usually obtained by precipitation from aqueous solutions. In their place it is also possible to use other alkaline earth metals of corresponding composition.

To obtain a satisfactory bleaching action even in washing at below 80° C., in particular in the range from 60° to 40° C., it is advantageous to incorporate bleach activators in the detergent, advantageously in an amount from 5 to 30% by weight, based on the $H_2O_2$-providing compound.

Activators for per-compounds which provide $H_2O_2$ in water are certain N-acyl and O-acyl compounds, in particular acetyl, propionyl or benzyl compounds, which form organic peracids with $H_2O_2$ and also carbonic and pyrocarbonic esters. Useful compounds are inter alia:

N-diacylated and N,N'-tetraacylated amines, e.g. N,N,N',N'-tetraacetyl-methylenediamine or -ethylenediamine, N,N-diacetylaniline and N,N-diacetyl-p-toluidine, and 1,3-diacylated hydantoins, alkyl-N-sulfonylcarboxamides, N-acylated cclic hydrazides, acylated triazoles or urazoles, e.g. monoacetylmaleohydrazide, O,N,N-trisubstituted hydroxylamines, e.g. O-benzoyl-N,N-succinylhydroxylamine, O-acetyl-N,N-succinylhydroxylamine, O-p-methoxybenzoyl-N,N-succinylhydroxylamine, O-p-nitrobenzoyl-N,N-succinylhydroxylamine and O,N,N-triacetylhydroxylamine, carboxylic anhydrides, e.g. benzoic anhydride, m-chlorobenzoic anhydride, phthalic anhydride and 4-chlorophthalic anhydride, sugar esters, e.g. glucose pentaacetate, imidazolidine derivatives, such as 1,3-diformyl-4,5-diacetoxyimidazolidine, 1,3-diacetyl-4,5-diacetoxyimidazoline and 1,3-diacetyl-4,5-dipropionyloxyimidazolidine, acylated glycolurils, e.g. tetrapropionylglycoluril or diacetyldibenzoylglycoluril, dialkylated 2,5-diketopiperazines, e.g. 1,4-diacetyl-2,5-diketopiperazine, 1,4-dipropionyl-2,5-diketopiperazine and 1,4-dipropionyl-3,6-dimethyl-2,5-diketopiperazine, acetylation and benzoylation products of propylenediurea or 2,2-dimethylpropylenediurea, the sodium salt of p-(ethoxycarbonyloxy)benzoic acid and of p-(propoxycarbonyloxy)benzenesulfonic acid and also the sodium salts of alkylated or acylated phenolsulfonic esters, such as p-acetoxybenzenesulfonic acid, 2-acetoxy-5-nonylbenzenesulfonic acid, 2-acetoxy-5-propylbenzenesulfonic acid or of isononanoyloxyphenylsulfonic acid.

The bleaching agents used can also be active chlorine compounds of the inorganic or organic type. Inorganic active chlorine compounds include alkali metal hypochlorites which can be used in particular in the form of their mixed salts and adducts on orthophosphates or condensed phosphates, for example on pyrophosphates and polyphosphates or on alkali metal silicates. If the detergent contains monopersulfates and chlorides, active chlorine will form in aqueous solution.

Organic active chlorine compounds are in particular the N-chlorine compounds where one or two chlorine atoms are bonded to a nitrogen atom and where preferably the third valence of the nitrogen atom leads to a negative group, in particular to a CO or $SO_2$ group. These compounds include dichlorocyanuric and trichlorocyanuric acid and their salts, chlorinated alkylguanides or alkylbiguanides, chlorinated hydantoins and chlorinated melamines.

Examples of additional assistants are: Suitable foam regulants, in particular if surfactants of the sulfonate or sulfate type are used, are surface-active carboxybetaines or sulfobetaines and also the abovementioned nonionics of the alkylolamide type. Also suitable for this purpose are fatty alcohols or higher terminal diols.

Reduced foaming, which is desirable in particular for machine washing, is frequently obtained by combining various types of surfactants, for example sulfates and/or sulfonates, with nonionics and/or with soaps. In the case of soaps, the foam inhibition increases with the degree of saturation and the number of carbon atoms of the fatty acid ester; soaps of saturated $C_{20}$–$C_{24}$-fatty acids, therefore, are particularly suitable for use as foam inhibitors.

The nonsurfactantlike foam inhibitors include possibly chlorine-containing N-alkylated aminotriazines which are obtained by reacting 1 mole of cyanuric chloride with from 2 to 3 moles of a mono- and/or dialkylamine having from 6 to 20, preferably 8 to 18, carbon atoms in the alkyl. A similar effect is possessed by propoxylated and/or butoxylated aminotriazines, for example products obtained by addition of from 5 to 10 moles of propylene oxide onto 1 mole of melamine and further addition of from 10 to 50 moles of butylene oxide onto this propylene oxide derivative.

Other suitable nonsurfactantlike foam inhibitors are water-insoluble organic compounds, such as paraffins or haloparaffins having melting points below 100° C., aliphatic $C_{18}$- to $C_{40}$-ketones and also aliphatic carboxylic esters which, in the acid or in the alcohol moiety, possibly even both these moieties, contain not less than 18 carbon atoms (for example triglycerides or fatty acid fatty alcohol esters); they can be used in particular in combinations of surfactants of the sulfate and/or sulfonate type with soaps for foam inhibition.

The detergents may contain optical brighteners for cotton, for polyamide, for polyacrylonitrile or for polyester fabrics. Examples of suitable optical brighteners are derivatives of diaminostilbenedisulfonic acid for cotton, derivatives of 1,3-diarylpyrazolines for polyamide, quaternary salts of 7-methoxy-2-benzimidazol-2′-ylbenzofuran or of derivatives from the class of the 7-[1′,2′,5′-triazol-1′-yl]-3-[1″,2″,4″-triazol-1″-yl]coumarins for polyacrylonitrile. Examples of brighteners suitable for polyester are products of the class of the substituted styryls, ethylenes, thiophenes, naphthalenedicarboxylic acids or derivatives thereof, stilbenes, coumarins and naphthalimides.

Further possible assistants or formulation aids are the conventional substances known to those skilled in the art, for example solubilizers, such as xylenesulfonates or cumenesulfonates, standardizing agents, such as sodium sulfate, enzymes or scent oils.

The detergents according to the invention can be for example pulverulent or liquid.

EXAMPLE 1

66.5 g (0.5 mol) of iminodiacetic acid are introduced into 100 g of water, and a pH of 9 is set with 105 g (1.05 mol) of 40% strength sodium hydroxide solution. A solution of 43.5 g (0.5 mol) of glycidamide in 50 g of water is then added dropwise at 60° C. in the course of 2 hours.

Complete conversion is ascertained with the aid of liquid chromatography after 5 hours of continued stirring at 60° C. The intermediate isolated by freeze drying, namely the disodium salt of isoserine-N,N-diacetic monoamide, has a melting point of above 300° C.

From the addition of 45 g (0.45 mol) of 40% strength sodium hydroxide solution the mixture is stirred at 100° C. for 4 hours until the evolution of ammonia has ceased and hence complete hydrolysis of the amide group has occurred.

This leaves 341 g of an approximately 40% strength yellow solution of the trisodium salt of 2-hydroxy-3-aminopropionic-N,N-diacetic acid. The melting point of the isolated salt is above 300° C.

The solution is brought to pH 2 with concentrated hydrochloric acid and added dropwise with ice-cooling to 3 times the volume of methanol. After 30 minutes of further stirring at 5° C. the precipitate is filtered off and washed with 70% strength aqueous methanol.

Drying under reduced pressure leaves 95 g ($\hat{=}$ 86% of theory) of 2-hydroxy-3-aminopropionic-N,N-diacetic acid having a melting point of 181°–184° C.

$C_7H_{11}NO_7$ (221.2) calculated C 38.01%, H 5.01%, N 6.33%; found C 37.92%, H 5.28%, N 6.15%.

EXAMPLE 2

66.5 g (0.5 mol) of iminodiacetic acid are introduced into 100 g of water, and a pH of 8.5 is set with 100 g (1 mol) of 40% strength sodium hydroxide solution. A solution of 59.5 g (0.5 mol) of sodium glycidate hemihydrate in 100 ml of water is then added dropwise at from 40° to 45° C. in the course of 1 hour. After a further 3 hours of stirring at 45° C. the end of the reaction is detected by chromatography.

An aqueous solution of the trisodium salt of 2-hydroxy-3-aminopropionic-N,N-diacetic acid is present.

The conversion into the free acid was carried out similarly to Example 1. Yield: 75% of theory.

EXAMPLE 3

A: preparation of 2-hydroxy-3-aminopropionic acid 85 g (1.25 mol) of concentrated 25% strength by weight aqueous ammonia are added dropwise at 50° C. to a solution of 119 g (1 mol) of sodium glycidate hemihydrate in 150 g of water in the course of 1 hour. This is followed by 5 hours of stirring at 50° C.

Unconverted ammonia and some of the solvent are removed under reduced pressure (aspirator), and the residue brought to pH 5 with glacial acetic acid. The resulting precipitate is filtered off and washed with methanol.

B: reaction with formaldehyde and hydrocyanic acid

The 85 g of 2-hydroxy-3-aminopropionic acid obtained on drying (≅ 81% of theory) (0.81 mol) are taken up in 200 g of water, and a pH of 8.5 is set with 40% strength sodium hydroxide solution. 43.7 g (1.62 mol) of liquid hydrocyanic acid and 165 g (1.65 mol) of 30% strength formaldehyde are simultaneously added dropwise at from 15° to 20° C. in the course of 2 hours.

2.5 hours of further stirring at 25° C. gives an aqueous solution of the nitrile of 2-hydroxy-3-aminopropionic-N,N-diacetic acid.

This nitrile is hydrolyzed at 100° C. with 1.65 mol of 40% strength sodium hydroxide solution. After 3.5 hours all the ammonia had been driven off.

From the resulting orange solution of the trisodium salt of 2-hydroxy-3-aminopropionic-N,N-diacetic acid it is possible to isolate the free acid as in Example 1 in a yield of 89%.

EXAMPLE 4

The solution obtained as described in Example 3 A is reacted as described in Example 3 B without isolation of the 2-hydroxy-3-aminopropionic acid and without acidification with glacial acetic acid with formaldehyde and hydrocyanic acid after the excess ammonia has been removed.

The alkaline hydrolysis gives an orange solution of the trisodium salt of 2-hydroxy-3-aminopropionic-N,N-diacetic acid, from which the free acid is isolated similarly to Example 1 in a 74% overall yield.

EXAMPLE 5

Example 3 is repeated using 1 mol of glycidamide in place of sodium glycidate hemihydrate.

Here the 2-hydroxy-3-aminopropionic acid was isolated as an intermediate in a 76% yield and further reacted as described in 3 B to give 2-hydroxy-3-aminopropionic-N,N-diacetic acid.

EXAMPLE 6

590 g of a 30% strength aqueous solution of the disodium salt of iminodiacetic acid (1.0 mol) are added dropwise at 55° C. with vigorous stirring to a solution of 87 g (1.0 mol) of glycidamide in 260 g of water in the course of 1.5 hours.

After a further 4 hours of stirring at 70° C. 103 g (1.03 mol) of 40% strength sodium hydroxide solution are added, and heating is continued at from 100° to 105° C. for 3.5 hours until no more ammonia is evolved. An aqueous solution of the trisodium salt of 2-hydroxy-3-aminopropionic-N,N-diacetic acid is then present, from which the free tricarboxylic acid is isolated similarly to Example 1 in an 87% yield.

EXAMPLE 7

0.2 mol of 2-hydroxy-3-aminopropionic acid dissolved in 50 ml of water and prepared as described in Example 3a) are brought to pH 11.5 with 10% strength by weight sodium hydroxide solution, and 0.4 mol of chloroacetic acid dissolved in water and neutralized with 10% strength by weight sodium hydroxide solution to pH 10 are added dropwise at such a rate that pH 9–10 can be maintained with 40% strength by weight sodium hydroxide solution.

Stirring is continued at 100° C. for 12 hours, and after cooling down the solution is brought to pH 2 with concentrated hydrochloric acid.

3 times the volume of methanol is then added dropwise with ice-cooling, stirring is continued for about 30 minutes, and the resulting precipitate is filtered off and washed with 70% strength by weight methanol. Drying leaves 40.2 g (≅91% of theory) of 2-hydroxy-3-aminopropionic-N,N-diacetic acid.

The tripotassium and triammonium salts obtained from the free 2-hydroxy-3-aminopropionic-N,N-diacetic acid each had melting points above 300° C.

Application properties

I. Determination of iron-complexing capacity

The inhibiting action of complexing agents on the precipitation of iron(III) hydroxide is determined by turbidimetric titration. The active substance (AS) under test is introduced initially and titrated in alkaline solution with iron(III) chloride solution until turbid.

The titration is carried out automatically by means of a Titroprozessor; in this titration, the light transmittance of the solution is monitored with a light guide photometer. The end point of the titration is indicated by the appearance of turbidity. The end point indicates the amount of bound iron and is a measure of the concentration of the complex formed relative to iron hydroxide.

In compounds having a dispersing action toward iron hydroxide, the end point is usually preceded by a discoloration.

The extent of the discoloration (caused by colloidally dispersed iron hydroxide) gives an indication of the dissociation tendency of the complex formed. A rough measure of this is the slope of the titration curve before the equivalence point is reached. The slope is measured in % transmission/ml of FeCl$_3$ solution. The reciprocal values thus indicate the concentration of the complex.

Method 1 mmol of the active substance (AS) under test is dissolved in 100 ml of distilled H$_2$O. The pH is set to 10 with 1 N NaOH solution and kept constant during the titration. The titration is carried out at room temperature with 0.05 M FeCl$_3$ solution at a rate of 0.4 ml/min.

The complexing capacity is expressed as:

$$\text{mol of Fe/mol of } AS = \frac{\text{ml of FeCl}_2 \text{ solution consumed}}{20}$$

or $$\text{mg of Fe/g of } AS = \frac{\text{ml of FeCl}_3 \text{ solution consumed}}{MW_{AS}} \times 2790$$

II. Test of sodium perborate stabilization in wash liquors

Principle

The hydrogen peroxide responsible for the bleaching action in detergent formulations which contain sodium perborate is catalytically decomposed by heavy metal ions (Fe, Cu, Mn). This is preventable by complexing the heavy metal ions. The peroxide-stabilizing action of a complexing agent is tested in terms of the residual peroxide content after a heavy metal containing wash liquor has been stored at elevated temperatures.

The hydrogen peroxide content is determined before and after the storage period by titration with potassium permanganate in acid solution.

The perborate stabilization test is carried out using two detergent formulations, and decomposition in the course of storage at elevated temperatures is effected by addition of heavy metal catalysts (2.5 ppm of a mixture of 2 ppm of $Fe^{3+}$, 0.25 ppm of $Cu^{2+}$ and 0.25 ppm of $Mn^{2+}$).

1. Phosphate-containing formulation Composition (in % by weight):
   19.3% of sodium $C_{12}$-alkylbenzenesulfonate (50% strength by weight aqueous solution)
   15.4% of sodium perborate . 4 $H_2O$
   30.8% of sodium triphosphate
   2.6% of copolymer of maleic acid and acrylic acid (50:50, average MW 50,000)
   31.0% of sodium sulfate, anhydrous
   0.9% of complexing agent according to the invention or of a comparative compound.

The detergent concentration is 6.5 g/l in water of 25° German hardness. The storage conditions are 2 hours at 80° C.

2. Reduced phosphate formulation Composition (in % by weight):
   15% of sodium $C_{12}$-alkylbenzenesulfonate (50% strength by weight aqueous solution)
   5% of adduct of 11 moles of ethylene oxide on 1 mole of tallow fat alcohol
   20% of sodium perborate . 4 $H_2O$
   6% of sodium metasilicate . 5 $H_2O$
   1.25% of magnesium silicate
   20% of sodium triphosphate
   31.75% of sodium sulfate, anhydrous
   1% of complexing agent according to the invention, or of a comparative compound.

The detergent concentration is 8 g/l in water of 25° German hardness. The storage conditions are 1 hour at 60° C.

III. Determination of calcium-binding power

Measurement principle

The inhibiting action of complexing agents or dispersants on the precipitation of calcium carbonate is determined by turbidimetric titration. The substance under test is introduced initially and titrated with calcium acetate solution in the presence of sodium carbonate. The end point is indicated by the formation of a calcium carbonate precipitate. By using an adequate amount of sodium carbonate it is ensured that the measurement provides a correct result even if the action is due not only to a complexing of calcium ions but also to a dispersing of calcium carbonate. For if the amount of sodium carbonate used is too small, there is a possibility that the dispersing power of the product is not fully utilized; in this case, the titration end point is determined by the precipitation of the calcium salt of the compound under test.

During the titration the change in light transmittance is monitored by means of a light guide photometer. In a light guide photometer, a light beam guided by a glass fiber into the solution is reflected at a mirror and the intensity of the reflected light is measured.

Reagents 0.25 M $Ca(OAc)_2$ solution
10% strength $Na_2CO_3$ solution
1 N NaOH solution
1% strength hydrochloric acid Procedure 1 g of AS in the form of the trisodium salt is dissolved in 100 ml of distilled $H_2O$. 10 ml of 10% strength $Na_2CO_3$ solution are then added. An automatic titration is carried out with 0.25M $Ca(OAc)_2$ solution added continuously at a rate of 0.2 ml/min at room temperature (RT) and a pH of 11, held constant during the titration, and at 80° C. at pH 10.

Calculation

Number of mg of $CaCO_3$/g of AS = consumption of $Ca(OAc)_2$ solution in ml × 25. In the automatic titration, the 1st break in the titration curve is the end point.

The results obtained are summarized in Table 1:

TABLE 1

| | Calcium binding power mg of $CaCO_3$/g of AS | | Iron-binding power | | | Perborate stabilization in [%] Detergent formulation | |
|---|---|---|---|---|---|---|---|
| | RT/pH 11 | 80° C./pH 10 | mol of $Fe^{3+}$ / mol of AS | mg of $Fe^{3+}$ / g of AS | % transmission (at break point) ml of $FeCl_3$ | 1 | 2 |
| 2-Hydroxy-3-aminopropionic-N,N—diacetic acid/$Na_3$ | 275 | 200 | 0.6 | 113 | 39 | 43.3 | 82.0 |
| Na triphosphate | 215 | 150 | | | | | |
| NTA/$Na_3$ | 350 | 250 | 0.25 | 54 | 11 | 24.5 | 32.5 |
| EDTA/$Na_4$ | 275 | 240 | 0.30 | 44 | 1.2 | 20 | 34.0 |

It follows from the results that the calcium-binding power, in particular that at room temperature, is comparable to that of the sodium salt of EDTA and substantially better than that of sodium triphosphate. Regarding the high value obtained for the sodium salt of NTA, the smaller molecular weight should be borne in mind as well. The binding power for iron is virtually twice as high as that of NTA and EDTA. The concentration of the complex formed, expressed in % transmission/ml of $FeCl_3$ solution, is many times higher than with the ethylenediaminetetraacetic acid complex and the nitrilotriacetic acid complex.

The particularly surprising effect is the excellent perborate stabilization of the relatively low molecular weight N-containing compound according to the invention.

If used as a builder substance in standard detergent formulations, good wash results are obtained, in particular as regards incrustation inhibition (as measured by the ash content).

We claim:

1. 2-Hydroxy-3-aminopropionic-N,N-diacetic acid, or a derivative thereof, of the formula I

where Y is a —COOH radical, which may be present in the form of an alkali metal, ammonium or substituted ammonium salt, a —COOR$^1$ radical where R$^1$ is alkyl of 1 to 4 carbon atoms, or a —CN radical, and X is hydroxyl, in which case the then resulting carboxyl may be present in the form of an alkali metal, ammonium or substituted ammonium salt, an —OR$^2$ radical where R$^2$ is alkyl of 1 to 4 carbon atoms, or an —NR$^3$R$^4$ radical where R$^3$ and R$^4$ are identical or different and each is hydrogen or alkyl of 1 to 4 carbon atoms.

2. A heavy metal and alkaline earth metal ion complexing agent of the formula I as claimed in claim 1 where Y is —COOH and X is —OH, and the carboxyl groups present may be in the form of an alkali metal, ammonium or substituted ammonium salt.

3. A process for preparing a compound of the formula I as claimed in claim 1 or 2, which comprises reacting a compound of the formula II

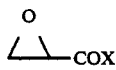

where X has the meanings indicated for the formula I, with a compound of the formula III

HN(CH$_2$-Y)$_2$   (III)

where Y has the meanings indicated for the formula I, in water, in an organic solvent or in a mixture thereof at from 10° to 80° C. and hydrolyzing any amide, ester and nitrile group present in the presence of an acid or base and as desired isolating the free acid or a salt conforming to the formula I.

4. A process for preparing a compound of the formula I as claimed in claim 1 or 2, which comprises reacting 1 mole of 2-hydroxy-3-aminopropionic acid, if desired in the form of an alkali metal salt, of an alkyl ester of 1 to 4 carbon atoms in the alkyl or of the amide, unsubstituted or mono- or disubstituted on the amide nitrogen by alkyl of 1 to 4 carbon atoms, in water, in an organic solvent or in a mixture thereof at from 0° to 100° C. with from 2.0 to 2.6 moles of a monohaloacetic acid, an alkyl monohaloacetate of 1 to 4 carbon atoms in the alkyl or monohaloacetonitrile in an alkaline medium or in the presence of an acid acceptor and hydrolyzing any amide, ester and nitrile groups present in the presence of an acid or base and as desired isolating the free acid or a salt conforming to the formula I.

5. A process for preparing a compound of the formula I as claimed in claim 1 or 2, where Y has the meanings indicated for the formula I other than —COOR$^1$ and X has the meanings indicated for the formula I, which comprises reacting 1 mole of 2-hydroxy-3-aminopropionic acid, if desired in the form of an alkali metal salt, of an alkyl ester of 1 to 4 carbon atoms in the alkyl or of the amide, unsubstituted or mono- or disubstituted on the amide nitrogen by alkyl of 1 to 4 carbon atoms, in water, in an organic solvent or in a mixture thereof with from 2.0 to 2.6 moles of formaldehyde at from 2.0 to 2.3 moles of liquid hydrocyanic acid at from 0° to 45° C. or with from 2 to 2.3 moles of an alkali metal cyanide at from 40° to 100° C. and hydrolyzing any amide, ester and nitrile groups present in the presence of an acid or base and as desired isolating the free acid or a salt conforming to the formula I.

6. A compound of the formula I where Y is —COOR$^1$, where R$^1$ is alkyl of 1 to 4 carbon atoms, or —CN, and X is —OR$^2$, where R$^2$ is alkyl of 1 to 4 carbon atoms, or —NR$^3$R$^4$, where R$^3$ and R$^4$ are identical or different and each is hydrogen or alkyl of 1 to 4 carbon atoms, as an intermediate for preparing a compound of the formula I as claimed in claim 2.

* * * * *